United States Patent
Doerr

(10) Patent No.: US 9,427,590 B2
(45) Date of Patent: Aug. 30, 2016

(54) IMPLANTABLE ELECTROSTIMULATION ASSEMBLY AND ADAPTER AND ELECTRODE LEAD OF THE SAME

(71) Applicant: BIOTRONIK SE & Co. KG, Berlin (DE)

(72) Inventor: Thomas Doerr, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 23 days.

(21) Appl. No.: 14/076,700

(22) Filed: Nov. 11, 2013

(65) Prior Publication Data

US 2014/0155951 A1 Jun. 5, 2014

Related U.S. Application Data

(60) Provisional application No. 61/732,950, filed on Dec. 4, 2012.

(51) Int. Cl.
*A61N 1/372* (2006.01)
*A61N 1/05* (2006.01)

(52) U.S. Cl.
CPC ............. *A61N 1/37211* (2013.01); *A61N 1/05* (2013.01)

(58) Field of Classification Search
CPC ...... A61N 1/05; A61N 1/37211; A61N 1/37; A61N 1/372
USPC ................................................. 607/9, 32, 116
See application file for complete search history.

(56) References Cited

U.S. PATENT DOCUMENTS

| 5,810,742 A * | 9/1998 | Pearlman ...................... 600/547 |
| 6,055,452 A * | 4/2000 | Pearlman ...................... 600/547 |
| 6,308,097 B1 * | 10/2001 | Pearlman ...................... 600/547 |
| 6,421,559 B1 * | 7/2002 | Pearlman ...................... 600/547 |
| 6,968,235 B2 | 11/2005 | Belden et al. |
| 7,016,726 B1 * | 3/2006 | Picardo et al. ...................... 607/5 |
| 7,240,833 B2 * | 7/2007 | Zarembo ...................... 235/385 |
| 7,429,920 B2 * | 9/2008 | Smythe et al. .......... 340/539.12 |
| 7,777,612 B2 * | 8/2010 | Sampson et al. .......... 340/426.1 |
| 7,983,763 B2 * | 7/2011 | Stevenson et al. ........... 607/115 |
| 8,180,129 B2 * | 5/2012 | Goetz .................. A61N 1/0551 382/128 |
| 8,209,029 B2 * | 6/2012 | Gray et al. ...................... 607/63 |
| 8,508,368 B2 * | 8/2013 | Potyrailo et al. .......... 340/572.1 |
| 8,509,876 B2 * | 8/2013 | Karmarkar ........... A61N 1/0534 324/318 |
| 8,734,339 B2 * | 5/2014 | Rao et al. ...................... 600/300 |
| RE45,030 E * | 7/2014 | Stevenson et al. ...... 340/539.12 |
| 8,798,698 B2 * | 8/2014 | Kim et al. ...................... 600/310 |
| 8,862,240 B2 * | 10/2014 | Goetz .................. A61N 1/0551 607/30 |
| 8,868,212 B2 * | 10/2014 | Gray ........................... 607/119 |

(Continued)

OTHER PUBLICATIONS

European Search Report and Notes to the European Search Report on European Patent Application No. EP 13 19 1854, dated Jan. 31, 2014 (6 pages).

*Primary Examiner* — Christopher A Flory
(74) *Attorney, Agent, or Firm* — Buchanan Ingersoll & Rooney PC

(57) ABSTRACT

An implantable electrostimulation assembly, including an electrostimulation device and an electrode lead that is connected to the electrostimulation device when in use, wherein the electrode lead has an optically readable electrode identification and a cable adapter is provided for the temporary insertion between the electrostimulation device and the electrode lead, the adapter comprising an optical pick up device for reading the electrode identification and an electrode identification transmission stage for transmitting the same to the electrostimulation device and/or to an assembly-external receiver.

20 Claims, 3 Drawing Sheets

(56) References Cited

U.S. PATENT DOCUMENTS

| | | | |
|---|---|---|---|
| 8,938,310 B2* | 1/2015 | Spotnitz et al. | 607/122 |
| 8,945,090 B2* | 2/2015 | Rassatt | A61N 1/05 600/372 |
| 2003/0149456 A1 | 8/2003 | Rottenberg et al. | |
| 2005/0033370 A1 | 2/2005 | Jelen et al. | |
| 2006/0058724 A1* | 3/2006 | Handfield et al. | 604/20 |
| 2007/0032832 A1* | 2/2007 | Feher | 607/32 |
| 2007/0083111 A1* | 4/2007 | Hossack et al. | 600/437 |
| 2007/0106169 A1* | 5/2007 | Fadem | 600/544 |
| 2007/0185390 A1* | 8/2007 | Perkins et al. | 600/300 |
| 2007/0191727 A1* | 8/2007 | Fadem | 600/544 |
| 2008/0065181 A1* | 3/2008 | Stevenson | 607/115 |
| 2009/0163981 A1* | 6/2009 | Stevenson et al. | 607/63 |
| 2009/0196472 A1* | 8/2009 | Goetz | A61N 1/0551 382/128 |
| 2009/0240308 A1* | 9/2009 | Feher | 607/60 |
| 2010/0063374 A1* | 3/2010 | Goodnow et al. | 600/365 |
| 2010/0069730 A1* | 3/2010 | Bergstrom et al. | 600/365 |
| 2010/0113898 A1* | 5/2010 | Kim et al. | 600/310 |
| 2010/0125176 A1* | 5/2010 | Hyde et al. | 600/300 |
| 2010/0161004 A1* | 6/2010 | Najafi et al. | 607/60 |
| 2010/0331932 A1* | 12/2010 | Stevenson et al. | 607/115 |
| 2011/0004276 A1* | 1/2011 | Blair et al. | 607/60 |
| 2011/0029043 A1* | 2/2011 | Frysz et al. | 607/60 |
| 2011/0118694 A1* | 5/2011 | Yodfat et al. | 604/500 |
| 2011/0160558 A1* | 6/2011 | Rassatt | A61N 1/05 600/377 |
| 2012/0310299 A1* | 12/2012 | Kaula et al. | 607/46 |
| 2012/0310300 A1* | 12/2012 | Kaula et al. | 607/46 |
| 2012/0316497 A1* | 12/2012 | Deutsch | 604/111 |
| 2014/0067011 A1* | 3/2014 | Kaula et al. | 607/59 |
| 2014/0155951 A1* | 6/2014 | Doerr | 607/32 |
| 2014/0236249 A1* | 8/2014 | Rao et al. | 607/6 |
| 2014/0243750 A1* | 8/2014 | Larsen et al. | 604/189 |
| 2014/0330357 A1* | 11/2014 | Stevenson et al. | 607/116 |
| 2014/0371819 A1* | 12/2014 | Goetz | A61N 1/0551 607/59 |

* cited by examiner

IMPLANTABLE ELECTROSTIMULATION ASSEMBLY AND ADAPTER AND ELECTRODE LEAD OF THE SAME

CROSS-REFERENCE TO RELATED APPLICATIONS

This patent application claims the benefit of U.S. Provisional Patent Application No. 61/732,950, filed on Dec. 4, 2012, which is hereby incorporated by reference in its entirety.

TECHNICAL FIELD

The present invention relates to an implantable electrostimulation assembly, comprising an electrostimulation device and an electrode lead that is connected to the electrostimulation device when in use. The present invention further relates to an electrode lead and a cable adapter of such an assembly.

BACKGROUND

Electrostimulation assemblies have been used especially for treating arrhythmia, but also within the scope of special treatments of other organs, such as, for example, the brain, for quite some time. Implantable systems for permanent and long-term use typically comprise an electrostimulation device which is positioned in a certain suitable location in the body, and an electrode lead which conducts the stimulation pulses to the treatment site. Because the available variety of electrostimulation devices and electrode leads—made by numerous different manufacturers—is diverse, and given that they may need to be combined for use, knowledge of the relevant design features and parameters of the electrode lead is required for the concrete treatment. Electrode leads are thus assigned electrode identifiers (e.g., type, serial number and the like), by means of which the relevant parameters can be determined, and which thus are transmitted either directly to the stimulation device or to a center of a clinic or cardiology practice preparing and managing the treatment.

The situation is similar when using systems for detecting the body's action potentials, in which the electrostimulation device is replaced by a discharge device connected to the electrode lead, and with combined discharge and stimulation assemblies. These are also covered by the field of the present invention.

Traditionally, electrode identifiers printed on the packaging of an electrode lead are read from the packaging during the initial use of the electrode lead and are entered manually in a work computer of the corresponding system, where they are processed to the extent that is required so as to ultimately be able to control the operation of the electrostimulation device in keeping with the parameters of the electrode lead.

In addition, assemblies in which the electrode identifiers are stored electronically on memory chips within the electrode lead are known, see U.S. Pat. No. 6,968,235, for example. However, such an additional electronic component in the lead increases the complexity of the design thereof and consequently results in higher costs, and in any case tends to lead to a greater likelihood of failure. Moreover, an interface for reading out the memory chip is required with an implantable device, so that it is far from possible to combine all standard devices with an accordingly equipped electrode lead.

The present invention is directed toward overcoming one or more of the above-identified problems.

It is therefore an object of the present invention to provide an electrostimulation assembly which is improved in terms of costs and reliability and which is to be produced universally from standard components. An object is achieved by an electrostimulation assembly having the characteristics of claim 1. Moreover, an electrode lead having the features of claim 11 and a cable adapter having the features of claim 14 are additionally provided. All of which are within the field of the present invention. Advantageous refinements of the present inventive concept are the subject matter of the respective dependent claims.

SUMMARY

The present invention encompasses the consideration to depart from the previously adopted course of storing electronically readable electrode identifiers in the electrode leads, and to dispense with any additional part in the permanently implanted assembly components which is used for the purpose of electrode identification. It further encompasses the concept/aspect to instead identify the electrode leads (and not the packaging thereof) in a machine readable manner, and particularly an optically readable manner, which also means to read the electrode identification directly from the lead. Another concept/aspect of the present invention is also that of providing a special part for this purpose, which prior to the permanent implantation of the assembly is temporarily incorporated therein, but is removed again after the function of the part has been fulfilled. According to another concept/aspect of the present invention, the electrostimulation device is replaced during aftercare, without likewise replacing a previously implanted electrode lead described above in the prior art and reading out the electrode identification thereof. Finally, according to the present invention a cable adapter is provided for this purpose for insertion between the electrostimulation device and the electrode lead, the adapter comprising read means for reading the electrode identification and transmission means for transmitting the same to the electrostimulation device and/or to an assembly-external receiver.

Because this cable adapter is not part of the permanently implanted system, the complexity of the adapter does not increase because of the proposed solution and is also not influenced by the system-immanent likelihood of failure. Because standard electronic parts can be used in the cable adapter, the increase in the system's costs associated with the provision of such an adapter is limited, and depending on the specific configuration, no increase in cost may be incurred at all for the electrode leads. The costs, however, are advantageously affected by the time savings and avoidance of error sources resulting from the elimination of human detection and input steps in preparation for the implantation.

In one embodiment of the present invention, the cable adapter is arranged together with the electrostimulation device in a common sterile packaging for shipment. As an alternative, the cable adapter may be arranged together with the electrode lead in a common sterile packaging for shipment. Another variant includes that the cable adapter is individually packaged for shipment and, in particular, designed so as to be re-sterilizable.

The electrode identification can preferably be read from the electrode lead mechanically, optically and/or electrically, and more particularly electromagnetically, or by means of radio frequency. The cable adapter then contains read means, which comprise mechanical, optical and/or electrical pick-up means, and more particularly electromagnetical pick-up means, or pick-up means of radio frequency.

Mechanical pick-up means detect electrode identifications which are implemented via a special shape or surface design of the electrode connector, such as a code via notches in the connector, for example.

Optical pick-up means detect optical characteristics of the electrode connector or of the electrode lead, or an optically readable identifier, such as a bar code, for example. For example, a camera, a CCD line or similar optical pick-up devices are typically used for this purpose. However, other optical pick-up means may be utilized.

Electrical pick-up means use a galvanic connection to the electrode lead, preferably via the plug contact which is already present, to detect electrical properties which are integrated in the electrode as identifiers, such as the read-out of a digital identifier in an identification chip in the electrode connector, for example. This can, for example, also be a characteristic electrical variable, such as a characteristic line impedance, capacitance or the like.

Electromagnetic and radio-frequency pick-up means use a contactless connection to the electrode lead to detect electrical properties which are integrated in the electrode as identifiers, such as the read-out of a digital identifier in an identification chip in the electrode connector, for example, or the read-out of an RFID or a comparable transponder chip, wherein the identification chip is supplied with power by the electromagnetic or radio-frequency energy.

In a further preferred embodiment, the electrode identification can be read out optically in a contactless manner and/or electrically in a contactless manner by the read means of the cable adapter.

Particularly preferred embodiments are possible in the latter case, in which the optically readable electrode identification includes a bar code or a letter/numeral combination and the read means of the cable adapter comprise a bar code scanner or a text scanner. If the system has a bar code-based design, a letter/numeral combination can be provided in addition to the bar code on the electrode lead so as to allow a direct examination, if necessary, by the medical staff entrusted with the overall assembly of the system.

Another embodiment includes the introduction of an RFID in the electrode connector which is polled in a contactless manner by the pick-up unit in the cable adapter by means of an RFID read method.

The optically readable electrode identification is preferably provided in or on a connector of the electrode lead. Deviating from this, however, it is also possible to mold, or join in another manner, a separate marker or a tag onto the lead proper to carry to the electrode identifier.

According to a further embodiment of the present invention, the transmission means of the cable adapter comprise a radio interface for telemetrically transmitting the electrode identification data to the electrostimulation device or for wirelessly transmitting the data to a corresponding radio interface of a treatment system. The specific technical design of the transmission means depends on the preferred mode—for example, telemetry transmission to the implantable medical device (IMD) or perhaps WLAN transmission to an input computer of the clinic system, or the like—and is defined by the conceptual considerations of the system manufacturer. The specification of the radio interface to be defined based on the respective decision does not go beyond the standard practice in the art and therefore does not require any further description herein.

According to a further embodiment, the cable adapter comprises an electrode identification converter for the code conversion of the read electrode identification according to the terminal specifications of the electrostimulation device and for transferring the recoded electrode identification to the transmission means for transmission to the electrostimulation device. This design is relevant, in particular, when providing the adapter in combination with the IMD because the electrode identification converter must be programmed with parameters of the IMD. In one embodiment of the latter design, transmission means are designed to transmit the electrode identification to the assembly-external receiver, this being a receiver which is located outside the assembly, so as to send both the read electrode identification and the recoded electrode identification data. The treatment center thus provides not only the data that has been recoded appropriately for the specific IMD, but additionally the original electrode identification data.

Further features, aspects, objects, advantages, and possible applications of the present invention will become apparent from a study of the exemplary embodiments and examples described below, in combination with the figures, and the appended claims.

DESCRIPTION OF THE DRAWINGS

Advantages and expedient characteristics of the present invention will additionally become apparent hereafter from the description of exemplary embodiments and concepts/aspects based on the figures. In the drawings.

DETAILED DESCRIPTION

Figure 1A:
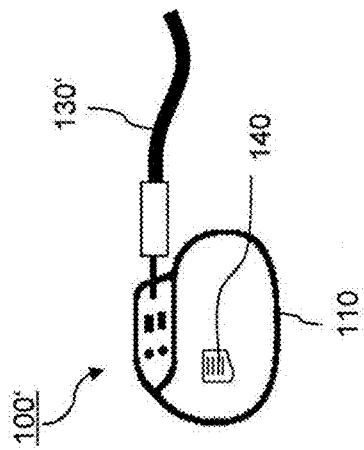
FIGS. 1A-1B show schematic diagrams of an embodiment of the present invention (temporary intermediate state or permanent implantation state)

FIG. 1A is a schematic illustration of an implantable electrostimulation assembly 100, the stimulation device of which in this example is a cardiac pacemaker 110. An electrode lead 130 is connected to the cardiac pacemaker 110 via a cable adapter 120. The electrode lead 130 has a connector plug 131, to the outer surface of which a bar code 133 is applied, in which the electrode identification data of the electrode lead is encoded. The cable adapter 120 is designed to read this bar code 133 and to transmit appropriately recoded data via a telemetry interface to the control unit of the pacemaker 110, where the data is processed for adjusting the pacemaker for the subsequent permanent implantation and stored in an electrode data memory 140.

Figure 1B:
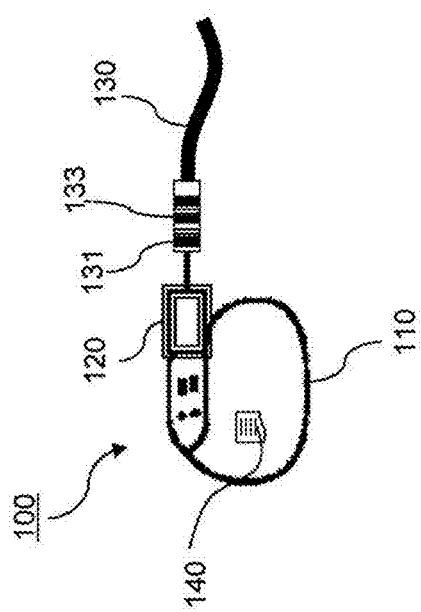

Before the stimulation assembly is implanted, the cable adapter 120 is removed again and the electrode lead 130 is permanently connected to the pacemaker 110, so that, in principle, the state of the assembly shown in FIG. 1B is created. However, by showing a different electrode lead 130', FIG. 1B is specifically intended to illustrate a further system option: When the electrostimulation device (the pacemaker), following an initial adjustment to a certain electrode lead based on the electrode identification data thereof, is ultimately connected to a different electrode lead (here denoted by numeral 130'), the electrode identification data of which cannot be transmitted in the afore-described manner to the control unit and the memory 140 of the pacemaker, the data that has been pre-processed and stored there will continue to apply until external reprogramming via a telemetrically connected programming device has been carried out. It is thus possible to achieve work and time savings during implantation even when using electrode leads not designed according to the present invention (for example, if the essential data thereof agrees with that of an electrode lead "read in" previously), wherein in any case the data of electrode leads not designed in keeping with the present invention can be input in the electrostimulation device in the conventional manner.

Figure 2:
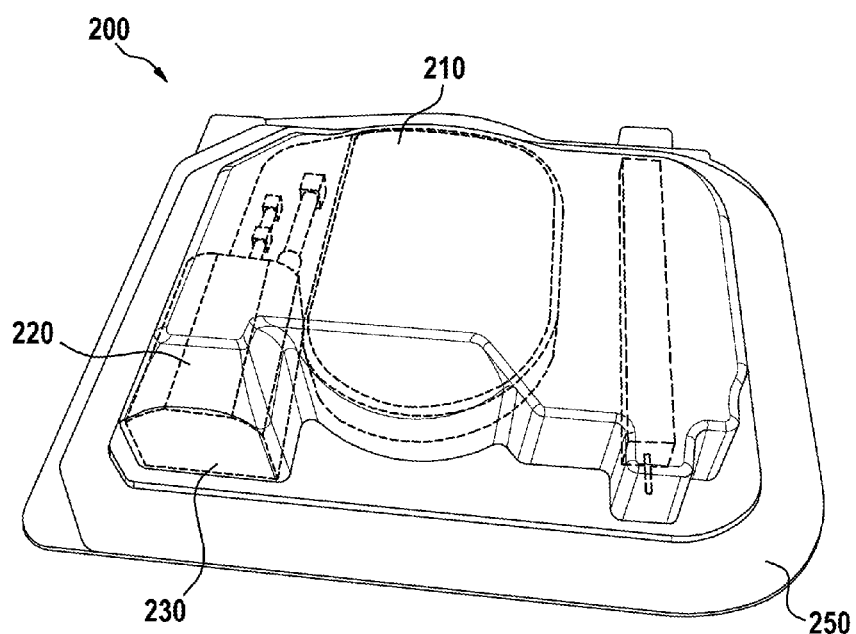
FIG. 2 is a perspective illustration of an embodiment of the present invention.

FIG. 2 shows a packaging unit 200 of a cardiac pacemaker 210, which together with a cable adapter 220, which is provided with a stable protective film 230, is accommodated in a sterile packaging 250 (so-called "internal blister", which has an outer packaging for shipping and transport). The packaging unit 200 can be used in the sterile clinic area and the cable adapter 220 is preassembled in the terminal region of the pacemaker 210, so that electrode leads (not shown) are introduced in the adapter without tools after the protective film 230 has been removed and the reading, measuring and transmission processes to be carried out by the cable adapter in cooperation with the pacemaker can be automatically triggered.

Figure 3:
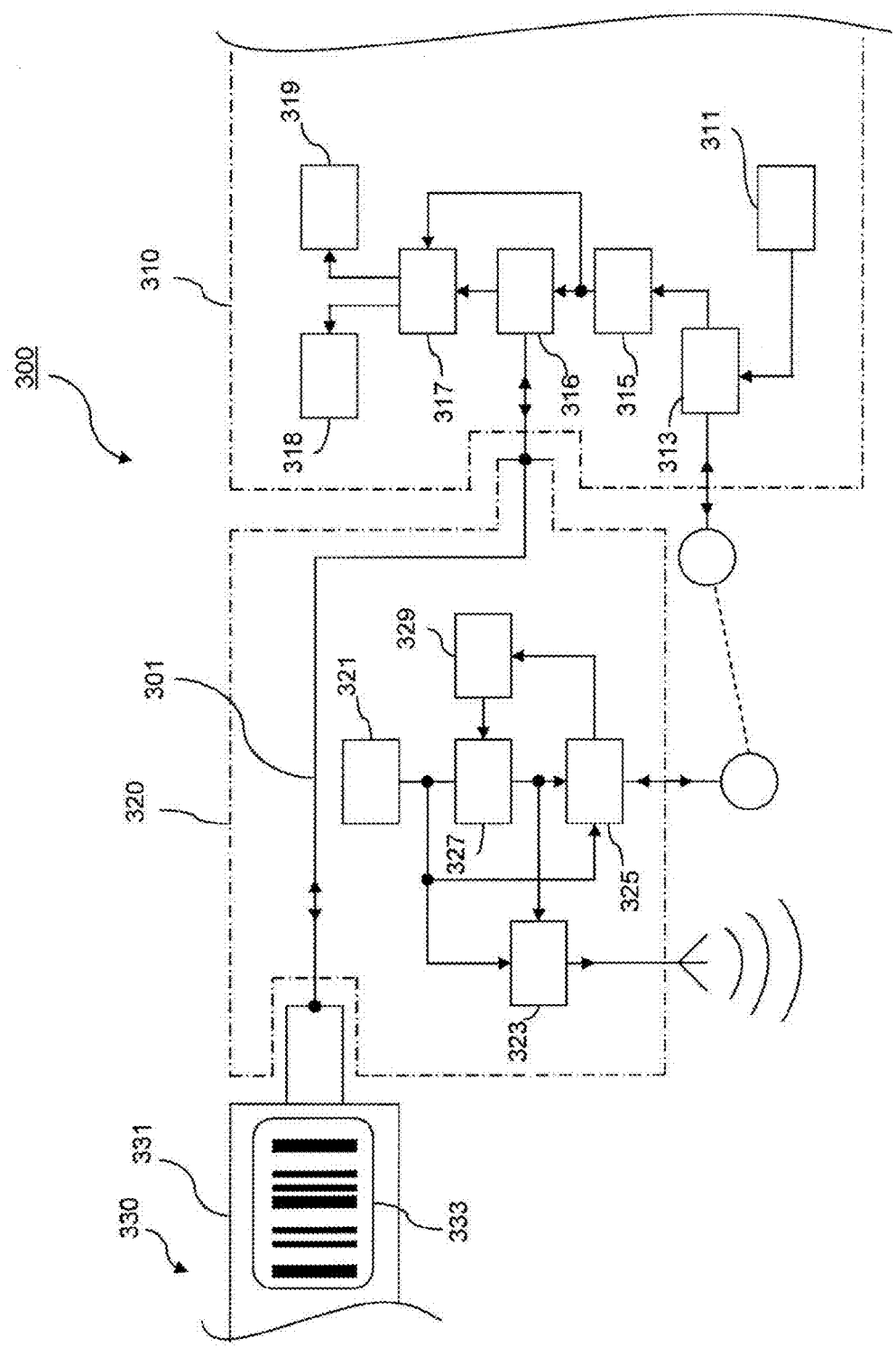
FIG. 3 is a schematic illustration of the design of an exemplary cable adapter in the manner of a functional block diagram.

FIG. 3 shows, in the manner of a functional block diagram, essential functional components of a pacemaker assembly 300 in the implantation preparation state, in which a cable adapter 320 is connected between a cardiac pacemaker 310 and an electrode lead 330. Here, only the components/functions of the cardiac pacemaker 310 which are essential in the context of the present invention are shown and described; otherwise, it can practically have any arbitrary conventional pacemaker design.

A bar code 333, which is read by a bar code scanner 321 of the cable adapter 320, is applied to a connector 331 of the electrode lead 330. On the output side, the bar code scanner 321 is connected to an electrode identification transmission stage 323, which transmits the electrode identification of the electrode lead 330 represented by the bar code via an antenna (not denoted separately) to a workplace computer of a treatment system used in the preparation for the implantation via WLAN.

On the output side, the bar code scanner 321 is also connected to a telemetry transceiver stage 325 and a code conversion unit 327. The telemetry transceiver stage 325 is used both to telemetrically transmit the electrode identification via a transmission coil (also not denoted separately) to the pacemaker 310, and to receive pacemaker data reaching a pacemaker data memory 329 of the cable adapter 320. Using this data, a pacemaker-specific code conversion of the electrode identification is carried out in the code conversion stage 327, and this recoded data is also transferred to the telemetry transceiver stage 325 for transmission to the pacemaker. The function of the code conversion of the electrode identification taking the pacemaker data into consideration could, of course, also be provided directly in the pacemaker; however, implementing the same in the cable adapter 320 makes it possible to transmit also the recoded data during the initialization procedure via the radio transmission stage 323 directly to the treatment system of the clinic or cardiology practice.

The pacemaker is provided with a pacemaker data memory 311 and a pacemaker-side telemetry transceiver stage 313 for supplying the pacemaker data and for transmitting the same to the cable adapter 320, and for receiving the electrode identification data and the recoded electrode identification data from the cable adapter 320. From the telemetry transceiver stage 313, the two sets of electrode identification data reach an electrode data memory 315 and are utilized in an electrode measuring stage 316 for measuring the electrode lead via the cable connection 301 which is temporarily established via the cable adapter 320. From the electrode measuring stage 316, the measurement results arrive via a processing stage 317 in a program memory 318 and a main memory 319 of the pacemaker 310 and are used as a basis for the operation of the pacemaker after the initialization phase has been concluded. The results of a direct processing step of the electrode data loaded from the electrode data memory 315 into the processing unit 317 also reach the main memory 319, to the extent this is required.

The implementation of the present invention is not limited to this example and concepts/aspects highlighted above, but is likewise possible in a plurality of modifications, which do not go beyond the standard practice in the art. In particular, the description of functions of one exemplary embodiment of the assembly according to the present invention provided in FIG. 3 in the spirit of an illustration can be modified in a wide variety of ways, for example, including the elimination of sub-functions, as will be appreciated by one skilled in the art.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

I claim:

1. An implantable electrostimulation assembly, comprising:
    an electrostimulation device comprising a control unit operably associated with a memory and a telemetry transceiver stage for receiving electrode identification data;
    an electrode lead that is connected to the electrostimulation device when in use, wherein the electrode lead has readable electrode identification;
    a cable adapter for the temporary insertion between the electrostimulation device and the electrode lead, the cable adapter comprising read means for reading the electrode identification and transmission means for transmitting the electrode identification data to the telemetry transceiver stage of the electrostimulation device and/or to an assembly-external receiver; and
    a programming device external to the electrostimulation device and telemetrically connected thereto;
    wherein the electrostimulation device is configured such that when the electrostimulation device, following an initial adjustment to the electrode lead based on the electrode identification data thereof, is connected to a different electrode lead, the electrode identification data of which cannot be transmitted, the readable electrode identification that has been pre-processed and stored within the control unit and the memory of the electrostimulation device continues to apply until external reprogramming via the programming device has been carried out.

2. The electrostimulation assembly according to claim 1, wherein the cable adapter is arranged together with the electrostimulation device in a common sterile packaging for shipment.

3. The electrostimulation assembly according to claim 1, wherein the cable adapter is arranged together with the electrode lead in a common sterile packaging for shipment.

4. The electrostimulation assembly according to claim 1, wherein the readable electrode identification is read mechanically, optically, and/or electrically, and the read means of the cable adapter have mechanical, optical, and/or electrical means.

5. The electrostimulation assembly according to claim 4, wherein the readable electrode identification is read out optically in a contactless manner and/or electrically in a galvanic or contactless manner by the read means of the cable adapter.

6. The electrostimulation assembly according to claim 4, wherein the readable electrode identification comprises a bar code or a letter/numeral combination and the read means of the cable adapter comprise a bar code scanner or a text scanner.

7. The electrostimulation assembly according to claim 6, wherein the optically readable electrode identification is provided on a connector of the electrode lead.

8. The electrostimulation assembly according to claim 1, wherein the transmission means of the cable adapter comprise a radio interface for telemetrically transmitting the electrode identification data to the electrostimulation device or for wirelessly transmitting the electrode identification data to a corresponding radio interface of a treatment center.

9. The electrostimulation assembly according to claim 1, wherein the cable adapter comprises an electrode identification converter for the code conversion of the read electrode identification according to terminal specifications of the electrostimulation device and for transferring the re-coded electrode identification to the transmission means for transmission to the electrostimulation device.

10. The electrostimulation assembly according to claim 9, wherein the transmission means for transmitting the electrode identification to the assembly-external receiver are designed to send both the read electrode identification and the re-coded electrode identification data.

11. The electrostimulation assembly according to claim 1, wherein the readable electrode identification is read electromagnetically.

12. The electrostimulation assembly according to claim 11, wherein the read means of the cable adapter have electromagnetical pick up means.

13. The electrode lead according to claim 1, wherein the readable electrode identification is accommodated in or on a connector.

14. The electrostimulation assembly according to claim 1, wherein the readable electrode identification is read by means of radio frequency.

15. The electrostimulation assembly according to claim 14, wherein the read means of the cable adapter have pick up means of radio frequency.

16. The cable adapter according to claim 1, which is individually packaged for shipment and more particularly designed so as to be re-sterilizable.

17. The electrode lead according to claim 1, wherein the readable electrode identification is read optically in a contactless manner and/or electrically in a galvanic or contactless manner.

18. The electrode lead according to claim 1, wherein the readable electrode identification comprises a bar code or letter/numeral combination.

19. An implantable electrostimulation assembly, comprising:
an electrostimulation device comprising:
a control unit operably associated with a memory; and
a first telemetry transceiver stage for receiving electrode identification data and transmitting electrostimulation device data;
an electrode lead having readable electrode identification, wherein the electrode lead is connected to the electrostimulation device when in use; and
a cable adapter for the temporary insertion between the electrostimulation device and the electrode lead, the cable adapter comprising:
read means for reading the readable electrode identification; and
transmission means comprising a cable connection and a second telemetry transceiver stage, wherein the second telemetry transceiver stage is used to both telemetrically transmit the electrode identification data via a transmission coil to the electrostimulation device and to receive the electrostimulation device data;
wherein the control unit adjusts the electrostimulation device based on the electrode identification data to generate an initial adjustment; and
wherein the electrode identification data generating the initial adjustment applies when a different electrode lead is connected to the electrostimulation device, but electrode identification data of which cannot be transmitted from the cable adapter to the control unit and the memory.

20. The electrostimulation assembly according to claim 19, wherein the read means of the cable adapter have mechanical, optical, and/or electrical means.

* * * * *